United States Patent [19]

Becker et al.

[11] Patent Number: 5,814,501
[45] Date of Patent: Sep. 29, 1998

[54] PROCESS FOR MAKING DUST-FREE ENZYME-CONTAINING PARTICLES FROM AN ENZYME-CONTAINING FERMENTATION BROTH

[75] Inventors: Nathaniel T. Becker, Burlingame, Calif.; Richard P. Crowley, Rochester, N.Y.

[73] Assignee: Genencor International, Inc., Rochester, N.Y.

[21] Appl. No.: 390,264

[22] Filed: Feb. 15, 1995

Related U.S. Application Data

[63] Continuation of Ser. No. 24,891, Mar. 1, 1993, abandoned, which is a continuation of Ser. No. 533,721, Jun. 4, 1990, abandoned.

[51] Int. Cl.$^6$ .............................. C12N 11/00; C12N 9/98; C12N 11/10; C11D 7/42
[52] U.S. Cl. .......................... 435/174; 435/176; 435/178; 435/187; 510/530
[58] Field of Search .................................. 435/187, 188, 435/174, 176, 178; 510/530

[56] References Cited

U.S. PATENT DOCUMENTS

| | | | |
|---|---|---|---|
| 2,059,983 | 11/1936 | Dent et al. ............................... | 51/278 |
| 2,561,392 | 7/1951 | Marshall ................................. | 117/100 |
| 3,117,027 | 1/1964 | Lindlof et al. .......................... | 118/303 |
| 3,382,093 | 5/1968 | Nack ...................................... | 117/100 |
| 4,233,405 | 11/1980 | Neubeck ................................. | 435/187 |
| 4,689,297 | 8/1987 | Good et al. ......................... | 435/187 X |
| 4,695,548 | 9/1987 | Cantor et al. ........................... | 435/179 |
| 4,707,287 | 11/1987 | Herdeman ................................ | 252/91 |
| 4,759,956 | 7/1988 | Amer er al. ............................. | 427/213 |
| 4,858,552 | 8/1989 | Glatt et al. ................................ | 118/19 |
| 4,876,198 | 10/1989 | Markussen .......................... | 435/187 X |
| 4,973,417 | 11/1990 | Falholt ..................................... | 252/95 |

FOREIGN PATENT DOCUMENTS

| | | |
|---|---|---|
| 0 193 829 | 9/1986 | European Pat. Off. . |
| 0 304 331 | 2/1989 | European Pat. Off. . |
| WO91/06638 | 5/1991 | WIPO . |

Primary Examiner—David M. Naff
Attorney, Agent, or Firm—Kirsten A. Anderson

[57] ABSTRACT

Substantially dust-free enzyme-containing particles are prepared by spray-coating solid particulate cores with a fermentation broth containing enzymes. Fermentation broths containing from 5% to 100% total enzyme solids and 4%–55% total solids content in the broth may be used. For broths containing 4%–31% total solids, enzyme and coating agents may be spray-coated so as to achieve a weight gain of 1%–24% w/w over the initial weight of the cores. For broths with 31%–55% total solids, a corresponding weight gain of 1%–100% may be achieved. The enzyme coated cores may be further coated with coating agents. The total dry weight added to the cores ranges from 1% to 19% in the absence of coating agents and 1% to 24% in the presence of coating agents when the lower range of total solids content is used. The total dry weight added to the cores ranges from 1% to 100% when the higher range of total solids content is used. These conditions are especially useful in the granulation of enzymes with very high specific activities, so that effective enzyme activity can be provided by adding low amounts of broth solids to the cores. Reduction in added solids is of significant economic benefit in reducing granulation costs.

3 Claims, No Drawings

PROCESS FOR MAKING DUST-FREE ENZYME-CONTAINING PARTICLES FROM AN ENZYME-CONTAINING FERMENTATION BROTH

This application is a continuation of application Ser. No. 08/024,891, filed Mar. 1, 1993, now abandoned, which is a continuation of application Ser. No. 07/533,721, filed Jun. 4, 1990, now abandoned.

FIELD OF THE INVENTION

The present invention relates to a novel procedure for making dry and dust-free enzyme granules from a fermentation broth containing the enzyme.

BACKGROUND OF THE INVENTION

Many commercially useful enzymes are produced by microorganisms, particularly bacteria, yeast, and filamentous fungi. These enzymes are especially useful in detergent and food applications. For example, enzymes useful in detergent applications, such as proteases, amylases, lipases, and cellulases, have been produced in a wide variety of microbial hosts. When enzymes are produced in a microbial host they are usually either secreted directly into the fermentation broth by the microorganism or released into the fermentation broth by lysing the cell. The enzyme can then be recovered from the broth in a soluble form by a number of techniques including filtration, centrifugation, membrane filtration, chromatography, and the like. The dissolved enzyme can be converted to a dry form from a liquid using techniques such as precipitation, crystallization, or spray-drying. A problem associated with dry enzyme preparations is that there is a high dust level associated with them, which can cause dermatologic distress to the manufacturer, consumer, or any other person handling the enzyme. It has been a desire in the art to treat these dry enzymes so as to reduce the hazard of dusting. To control dusting and increase particle size, dry enzymes are often granulated by various means known by those skilled in the art. Various enzyme formulations and processes for these preparations have been developed in an effort to alleviate the dusting problem. For example, German Patent No. 21 37 042 discloses a process in which an extrudable enzyme containing formulation is extruded through a die onto the revolving plate of a spheronizing device to form spherical particles of the enzyme-containing formulations which are optionally coated with a material designed to prevent dusting.

In U.S. Pat. No. 4,087,368, there is disclosed an enzyme granule formulation in which rods or spheres of an enzyme in admixture with magnesium alkyl sulfate and ethylene oxide are provided.

U.S. Pat. No. 4,016,040 discloses a method for the preparation of free-flowing substantially dust-free, spherical enzyme-containing beads prepared by blending a powdered concentrate of the enzyme with a binder in molten form and spraying droplets of the blend through a spray nozzle into cool air to solidify the droplets and form the beads.

In U.S. Pat. No. 4,242,219, there is claimed a process for the preparation of enzyme-containing particles prepared by mixing the dry enzyme with a hydrophilic organic cohesive material, a building agent, or a mixture regulating agent and mechanically dividing it into particles of the desired size and shape which are then coated with a water repellent material.

Another type of granular enzyme formulation is described in U.S. Pat. No 4,009,076. This formulation is prepared by mixing the dry enzyme with a solid nonviable substance and optionally a cohesive organic material as binder to form an enzymatically active core. An enzyme slurry containing the cohesive organic material can be sprayed onto, for example, sodium tripolyphosphate and the cohesive organic material sprayed onto it with subsequent extrusion through a die. The enzyme-containing granule is sprayed with an aqueous solution containing a plasticized organic resin, then dried.

A process is described in GDR Pat. 0 151 598 in which sodium tripolyphosphate is sprayed with an aqueous fermentation broth and agglomerated in a cyclone apparatus. The agglomerates are removed from the cyclone apparatus while still wet and placed in a mechanical blender with a drying detergent formulation and intensively mixed.

In British Pat. No. 1,483,591,there is described a process for coating water soluble or water dispersible particles, including enzyme particles, using a fluidized bed reactor. This reference involves a dust-free coating technique for enzyme particles which have been granulated by other processes such as prilling or spheronizing.

In U.S. Pat. No. 4,689,297 there is described a method for preparing dust-free enzyme involving dissolving or suspending dry enzyme in solution to make a slurry with 15%–30% total solids, of which at least 30% w/w of the solids is enzyme, spraying it on a hydratable core, and then coating it with macromolecular material, so as to increase the dry weight of the core by between 25 and 55%.

Advances in enzyme engineering and selection have led to the development of enzymes which are very active on a specific weight basis, thereby substantially reducing the percentage of total added enzyme broth solids needed in producing an effective granular product. Furthermore, proper selection of core and coating materials significantly reduces the levels of coating agents required for adequate encapsulation and dust control.

It is desirable to be able to produce a dry dust-free product with a relatively low percentage of total weight as enzyme, especially with enzymes of high specific activity.

With these more active enzymes, it is also sometimes desirable to feed the spray-coater with enzyme solutions of very high solids concentrations. This can occur for several reasons: (1) proteases of high specific activity are often more subject to autolysis, and the addition of large percentages of solid stabilizer compounds may be needed to achieve high process yields; (2) in general, it is most economical to remove as much water as possible from the enzyme solution prior to spray-coating by methods such as ultrafiltration, thereby reducing the batch cycle time in the spray-coater; (3) it is sometimes desirable to add processing aids such as binders or powders into the enzyme concentrate to reduce product dustiness or help prevent excessive agglomeration of the granules. For any of these reasons, it may be desirable to provide a fermentation broth containing between about 31% and 55% solids on a dry weight basis, so long as it is not too viscous to be pumped through a spray nozzle.

This invention achieves these and other desirable objectives in a cost-effective, efficient, and safe manner.

SUMMARY OF THE INVENTION

It has surprisingly been discovered that a dry dust-free enzyme particle can be produced from fermentation broth by the following method:

a) introducing a particulate, hydratable core material into a fluidized bed spray-coater and maintaining the core particles suspended in the reaction chamber: optionally, producing, building up, or otherwise modifying the core particles in a fluidized bed spray-coater and maintaining the core particles suspended in the reaction chamber;

b) providing a fermentation broth containing from about 5% to about 100% w/w of the total solids therein of a water soluble or dispersible enzyme produced in the fermentation broth and a total solids content of 4–31% w/w of the fermentation broth such that the broth has a viscosity of 10–5,000 cps at room temperature; and c) spraying the broth onto the core and evaporating the liquid to leave the solids coated on the core, such that the fermentation broth solids added to the core provides a total dry weight gain of 1%–19% w/w over the initial weight of the core, and optionally the additional step of:

d) spraying a coating agent over the product of step (c) and evaporating the liquid to leave the coating agent over the solids of (c) such that the total solids consisting of fermentation broth solids plus coating agent added to the core provides a total dry weight gain of 1%–24% w/w over the initial weight of the core.

Also disclosed is a similar process in which the fermentation broth has a total solids content of 31% to 55% w/w. In this process the total dry weight gain of the core particles is from 1% to 100% w/w. The enzyme-containing particles prepared by these processes are included in this invention.

DETAILED DESCRIPTION OF THE INVENTION

The method of the present invention is carried out in a fluidized bed spray-coater. Typically, such a device comprises a fluidized bed dryer consisting of a conical product chamber that has a porous grid on the bottom and is open on the top to be put up against a cylindrical or conical shaped expansion chamber of a larger diameter than the product chamber; a filter to collect dust and help air flow is placed at the far end of the expansion chamber and one or more spray nozzles are located within the chamber to apply the solution to the core. In operation, as the velocity of air passing up through the chamber is increased, a point is reached where particles resting on the porous grid are suspended in the air flow as a fluid, hence the terms "fluidization" and "fluidized bed dryer". The particles are lifted by the upward force of the air out of the product chamber into the expansion chamber where the air expands and the upward force per unit of area is reduced. This allows the particles to fall back into the product chamber and start the cycle over.

The initial step in the method involves introducing a particulate, hydratable core material into the reaction chamber of the fluidized bed dryer and suspending the particles therein on a stream of air. The core particles preferably are composed of a highly hydratable material, i.e. a material which is readily dispersible or soluble in water. The core material should either disperse (fall apart by failure to maintain its integrity) or dissolve by going into a true solution. Clays (bentonite, kaolin), non pareils, and agglomerated potato starch are considered dispersible. Non pareils are spherical particles consisting of a solid nucleus that has been rounded into a spherical shape by binding layers of powder and crystallized solute, generally starch and sugar, to the nucleus in a rotating spherical container and are preferred. Non pareil particles are often called "seeds".

Salt particles (NaCl crystals, NaCl rock salt, NaHCO$_3$) are considered soluble. Also suitable are agglomerated trisodium citrate, pan crystallized NaCl flakes, bentonite granules and prills, bentonite/kaolin/diatomaceous earth disk-pelletized granules, and sodium citrate crystals. The core particle is of a material which is not dissolved during the subsequent spraying process and is preferably of a particle size from 150 to 2,000 microns (100 mesh to 10 mesh on the U.S. Standard Sieve Series) in its longest dimension.

By fermentation broth is meant the liquid in which the enzyme is produced by fermentation of a microorganism. The broth may be modified by deleting or adding material, e.g. filtration of cell solids or addition of binders, salts, pigments, plasticizers, and fragrances, however, it still contains the enzyme. It also may be concentrated or purified by removal or substitution of a portion of the liquid material, by such processes as ultrafiltration, extraction, and chromatography.

Enzymes suitable for use in this method are those which are soluble or dispersible in the fermentation broth they are produced in, and from which the volatile components of the fermentation broth can be removed to leave a residual layer of enzyme on the surface of the core material. Suitable enzymes include, for example, proteases (bacterial, fungal, acid, neutral, or alkaline), amylases (alpha and beta), lipases, and cellulases. The enzyme is present in the broth at from about 5% to about 100% w/w of total solids, and fermentation broth solids range from about 0.5% to about 95.5% w/w of total solids in the fermentation broth, with any remaining solids comprising added metallic salts, sugars, pigments, binders, stabilizers, plasticizers, and fragrances such that total solids represent 4%–31% w/w of the fermentation broth. The broth, including any optional metallic salts, sugars, pigments, binders, stabilizers, plasticizers, and fragrances, must have a viscosity low enough to be pumped and atomized for effective spray-coating (typically 10 to 5,000 cps at room temperature). The broth solids and enzymes are applied to the surface of the core material by fluidizing the core particles in a flow of air whereupon a broth containing the enzyme and other solids is then atomized and sprayed into the expansion chamber of the spray-coater. The atomized droplets contact the surface of the core particles leaving a film of the solids adhering to the surface of the particles when the water and other volatiles are evaporated.

Airflow is maintained upwards and out the top of the expansion chamber through a filter. The filter may be located inside or outside of the unit, or may be substituted for by a scrubber or cyclone. This filter traps fine dried particles which contribute to dust. Fluidized bed spray-coaters that have this filter typically have automatic shakers which shake the filter to prevent excessive restriction of the air flow. In a preferred embodiment, the shaker unit is turned off during the last 5 minutes of operations, thus reducing the dust content of the product due to release of fines trapped within the filter. In another preferred embodiment, the filter is located outside the unit or substituted by a scrubber or cyclone.

When recovering fermentation broth enzymes, the broth may be treated in various ways to achieve desired results. For example, the broth may be filtered to remove cells and cell debris or to remove microorganisms to yield a sterile product. The broth may be concentrated to achieve the desired total solids concentration of about 4% to about 31% w/w of the broth. Further, as mentioned above, salts, stabilizers, etc., can also be added as desired, and the enzyme may be concentrated or purified as desired. It is further a preferred embodiment of the invention that the weight gain of the solids in the broth applied to the core over the initial dry weight of the core is about 1% to about 19% w/w.

In another distinct preferred embodiment, the desired total solids concentration is about 31% to about 55% w/w of the broth. In this embodiment, the weight gain of the solids in the broth applied to the core over the initial dry weight of the core is about 1% to about 100% w/w.

Handling the enzyme in liquid form in the fermentation broth has the advantage of lowering the possibility of dermatologic contact due to dusting and produces a product which is dust-free and minimizes losses due to any extra step of drying, since the drying process is confined to a single, well-contained reactor.

When sufficient enzyme is applied to the core particles to provide the desired enzyme activity, the enzyme coated particles, while still suspended in the reaction chamber of the coater or later reintroduced therein, are coated with a layer of a water soluble or water dispersible coating agent. This is accomplished in a manner similar to that used for application of the enzyme/solids coating. Suitable coating agents include, for example, fatty acid esters, gum arabic and other natural gums, alkoxylated alcohols, polyvinyl alcohols, ethoxylated alkylphenols and more specifically, polyethylene glycols (PEG) (molecular weight (MW) 300 to 20,000), linear alcohol alkoxylates (MW 1,450 to 2,670), polyvinyl acetate phthalate (PVAP), polymeric nonylphenyl ethoxylates (MW 1,975 to 4,315) dinonyl phenyl ethoxylate (average MW 6,900), hydroxypropylmethyl cellulose, and other modified celluloses. Other coating agents include sugars, starches, salts, titanium dioxide, and other sealants, stabilizers, release agents, binders or pigments. The net result of the process is to provide an enzyme coated core particle having a layer of the coating agent on its surface to provide the desired dust-free enzyme-containing particle. When a fermentation broth with about 4% to about 31% w/w total solids content is used, the total weight gain of solids versus the initial core is preferably from about 1% to about 24% w/w when a coating is used, and preferably from about 1% to about 19% w/w when a coating is not used. When a fermentation broth with about 31% to about 55% w/w total solids content is used, the total weight gain of solids versus the initial core is about 1% to about 100% whether a coating is used or not.

The dust-free enzyme particles of the present invention can be used wherever enzymes are needed in a dry system. Thus, they can be used as additives to dry detergent formulations, for removing gelatin coatings on photographic films to aid in silver recovery, in the digestion of wastes from food processing plants for nitrogen recovery, in denture cleansers for removing protein bound stains, in food preparation, and as a processing aid in waste water treatment.

The following examples are representative and not intended to be limiting. One skilled in the art could choose other enzymes, broths, cores, and coating agents based on the proportions of ingredients taught herein.

PREFERRED EMBODIMENTS

EXAMPLE 1

Lab-Scale Spray-Coating of FNA Protease Onto Non Pareils, With Gum Arabic Coating Agent.

A WSG-5 fluidized-bed granulator was charged with 3800 grams of −35/+40 mesh non-pareil cores or seeds and heated to 60° C. and fluidized. A two liter aqueous protease ultrafiltration concentrate containing 3.8% w/w enzyme and 10.5% w/w total solids (36.2% w/w of total solids were enzyme) was sprayed onto the suspended cores at a 95° C. inlet temperature and a 40°–50° C. outlet temperature. The spray rate was about 45 ml/minute (min) and enzyme coating or plating took 37 minutes, resulting in an estimated weight gain of 210 grams, or 5.5% w/w. At this point, 230 grams of material was removed for subsequent analysis, leaving 3780 grams of enzyme coated active cores. A coating agent solution containing 60 grams gum arabic in 600 ml water was applied at 40 ml/min; the entire granulation or coating lasted 56 minutes. The final product weighed approximately 3840 grams, representing a 1.6% increase over the enzyme-plated cores, and a 7.2% net increase in weight over the initial core weight.

EXAMPLE 2

Lab-Scale Spray-Coating of FNA Protease Onto NonPareils, With PEG 8000 and $TiO_2$ Coating Agents.

A WSG-5 fluidized bed granulator was charged with 5000 grams of −20/+40 mesh non pareil cores or seeds which were fluidized. A 1786 ml aqueous protease concentrate containing 3.8% w/w enzyme and 10.5% w/w total solids (as in Example 1) was sprayed onto the cores at an inlet temperature of about 70° C. and an outlet temperature of 40°–50° C. The weight gain due to the protease was 188 grams, or 3.8% w/w. A coating agent solution containing 150 grams PEG 8000 and 250 grams $TiO_2$ in 1 liter of water was sprayed on the enzyme-coated non pareils which were dried.

The final product weighed 5560 grams, representing an 11.2% increase over the initial core weight.

EXAMPLE 3

Spray-Coating of Lipase Onto Non Pareils, With Hydroxypropylmethylcellulose (Opadry White) Coating Agent.

A Uni-Glatt laboratory fluidized bed spray-coater was charged with 960 grams of −20/+40 mesh non pareil cores or seeds which were fluidized. A 1700 ml aqueous lipase concentrate of 6.9 gram/liter lipase with 4.9% total solids was sprayed onto the non pareil cores at an inlet temperature of 50°–66° C. and an outlet temperature of 38°–42° C. and an atomization pressure of 2.5 bar. Enzyme was 14.1% of total solids. The enzyme-coated cores weighed 962 grams, an increase of 5.0% w/w. After enzyme layering and reactor cleaning, a coating agent solution containing 70 grams Opadry White, a name used in trade for hydroxypropylmethylcellulose, and 400 grams water was sprayed onto the enzyme coated active cores, resulting in coated product weight of 1032 grams, a net increase of 12.7% w/w. This product contained 78% of the original active lipase in the feed concentrate. The product granules lost no activity after incubation at 26.7° C. and 80% relative humidity over two weeks.

EXAMPLE 4

Spray-Coating of Detergent Cellulase Onto Non Pareils, Without Coating Agent.

A Uni-Glatt laboratory fluidized-bed spray-coater was charged with 1000 grams of −20/+40 mesh non pareil cores or seeds which were fluidized. An 840 ml aqueous cellulase concentrate containing 172 gram/liter enzyme and 24.7% total solids was sprayed at an inlet temperature of 50°–64° C. and an outlet temperature of 38°–46° C. at a spray-rate of about 10 ml/min. Enzyme represented 69.6% of total broth solids. At the end of the run, 1143 grams of product were recovered, representing a 14.3% w/w increase over the non pareil cores. Recovery of active enzyme was 98.8% of the ultrafiltration concentrate feed, as measured using bFPU units.

EXAMPLE 5

Large-Scale Spray-Coating of FNA Protease Onto Non Pareils, With PEG 8000 and TiO$_2$ Coating Agents.

A modified Aeromatic S-8 fluidized bed granulator was used for a large-scale spray-coating run. The coater was loaded with 681.8 kg (1500 lbs) non pareil seeds of −20/+40 mesh. The bowl was raised into place and the cores fluidized with 65° C. inlet air until the outlet air temperature reached 45° C. A 100.4 kg aqueous protease enzyme concentrate containing 5.94 w/w active enzyme and 21.3% w/w total solids was sprayed onto the cores using a 1.8 mm multiple-head Schlick nozzle at 4 bar atomization air pressure. The outlet air temperature was maintained between 40° and 50° C. Enzyme represented 27.9% w/w of total feed solids. Enzyme coating or layering took about 80 minutes, excluding a 15 minute shutdown to examine the product in the bowl for coating uniformity. The application rate was about 1.2 liters per minute. By calculation, this represented a weight gain of 3.1% w/w over the cores. The bowl was temporarily removed and the machine was cleaned. Over-coating was then applied to the enzyme granules in the same dryer/coater unit. The coating agent solution consisted of 123.6 kg of tap water heated to 50° C., in which 67.4 kg PEG 8000 and 33.7 kg TiO$_2$ were dissolved or suspended to give a 150 liter solution. The enzyme coated granules were fluidized and heated to 45° C. as before. Atomization air pressure was held at 4 bar and outlet air temperature varied between 40° C. and 50° C. The total coating run time was 136 minutes with an application rate of about 1.1 liter per minute. After coating, the product was dried for four minutes until the outlet temperature reached 48° C., then cooled for 14 more minutes until outlet temperature reached 32° C. The bowl was removed and the product sieved to a −16/+40 cut. The mass balance is shown in Table 1. The final product represented a net increase of 13.0% w/w over the core weight using the actual product weight or a net increase of 17.9% w/w over the core weight using the theoretical sum of ingredient weights. Product dust was extremely low. The product granules produced 0.3 milligrams total dust and 2.42 micrograms protease dust per 60 gram sample when subjected to a 40 minute standard elutriation test.

TABLE 1

| Raw Materials | Dry Weight (kg) | Percent of Feed | Pure Enzyme (kg) | Percent of Feed |
|---|---|---|---|---|
| Cores | 681.8 | 84.8 | — | — |
| Enzyme Solution (5.94% w/w enzyme) | 21.4 | 2.7 | 5.96 | 100.0 |
| PEG 8000 | 67.4 | 8.4 | — | — |
| TiO$_2$ | 33.7 | 4.2 | — | — |
| TOTAL | 804.3 | 100.0 | 5.96 | 100.0 |
| End Products (0.68% w/w enzyme) | | | | |
| Product (+40 mesh) | 769.7 | 95.7 | 5.24 | 87.9 |
| Fines (−40 mesh) | 2.0 | 0.2 | 0.01 | 0.2 |
| TOTAL | 771.7 | 95.9 | 5.25 | 88.1 |

EXAMPLE 6

Large-Scale Spray-Coating of Alkaline Protease Onto Non Pareils, With Hydroxypropylmethylcellulose and TiO$_2$ Coating Agents.

A WSG 300 granulator is charged with 700 kg of non pareil seeds or cores of −20/+40 mesh and the cores are fluidized. A 36 kg concentrated aqueous solution containing 10% w/w protease and 29% w/w total solids, with enzyme 34.5% w/w of total solids, is sprayed onto the fluidized cores. Spraying is continued until the total charge weighs 710.4 kg, which represents a 1.49% w/w gain over the initial core weight. A coating agent solution consisting of 3.5 kg hydroxypropylmethylcellulose 3.5 kg TiO$_2$, and 30 kg water is sprayed on the fluidized enzyme coated cores. The total product weight is 717.4 kg, which represents a total weight gain of 2.49% w/w.

EXAMPLE 7

Large-Scale Spray-Coating of Cellulase Onto Non Pareils, With PEG 20,000 and TiO$_2$ Coating Agents.

A WSG 300 granulator is charged with 700 kg non pareil seeds of −20/+40 mesh and the seeds are fluidized. A 334 kg aqueous concentrated cellulase solution containing 26% w/w cellulase and 39% w/w total solids, with enzyme 66.7% w/w of total solids, is sprayed onto the fluidized cores. Spraying continues until the total charge weighs 830.3 kg, which represents a gain of 18.6% w/w over the initial core weight. A coating agent solution consisting of 18.5 kg PEG 20,000, 18.5 kg TiO$_2$, and 100 kg water is sprayed on the fluidized enzyme coated seeds. The total product weight is 867.3 kg, which represents a total weight gain of 23.9% w/w.

EXAMPLE 8

Spray-Coating of High Solids Protease Onto Non Pareils, With PEG 8000 and TiO$_2$ Coating Agents.

A Glatt GPCG-5 fluidized bed granulator is charged with 10.0 kg non pareil seeds. A 4766 gram aqueous *Bacillus lichenformis* subtilisin ultrafiltration concentrate containing 20% w/w enzyme solids and 32% w/w total solids, with enzyme 63% w/w of total solids, is sprayed onto the fluidized cores at a rate of 85 g/minute and an atomization air pressure of 2.5 bar. The inlet air temperature is about 70° C. and the outlet temperature is about 48° C. A coating solution of 2000 grams PEG 8000 and 500 grams TiO$_2$, suspended in 10 liters of water, is then sprayed onto the enzyme-coated cores under the same conditions. The final coated product weighs 14.0 kg, a weight gain of 40% w/w.

EXAMPLE 9

Spray-Coating of High Solids Cellulase Concentrate Onto Non Pareils, With PEG 8000 and TiO$_2$ Coating Agents.

A Uni-Glatt laboratory spray-coater is charged with 600 grams non pareil seeds. At an inlet temperature of 60° C., an outlet temperature of 42° C., and an atomization air pressure of 3 bar, an aqueous cellulase concentrate of 455 grams containing 30.3% w/w enzyme and 39.5% w/w total solids, with enzyme 77% w/w of total solids, is sprayed onto the fluidized cores, increasing the weight of the cores to 780 grams, a 29.7% w/w increase. A coating solution containing 200 grams PEG 800 and 200 grams TiO$_2$ in 1.5 liters of water is sprayed on the cores under the same conditions. The harvested product weighs 1180 grams, a net increase in weight of 97% over the original cores.

EXAMPLE 10

Spray-Coating of Protease Concentrate With Added Salts Onto Non Pareils, With Gum Arabic and TiO$_2$ Coating Agents.

A Uni-Glatt laboratory spray-coater is charged with 800 grams non pareil seeds. A 500 ml aqueous protease concentrate weighing 520 grams and containing 8% w/w protease and 24% w/w total solids is modified by dissolving 100 grams of stabilizer salts in the concentrate. These additions increase the solution volume to 540 ml and the solution weight to 620 grams. The modified concentrate, with 6.7% w/w enzyme solids and 36.3% w/w total solids, is sprayed onto the fluidized cores at an inlet temperature of 50° C., an outlet temperature of 40° C., and an atomization air pressure of 3.5 bar. This increases the product weight to 1025 grams, a 28.1% w/w increase over the core weight. A coating solution containing 120 grams gum arabic and 60 grams TiO$_2$ is then sprayed over these cores resulting in a final product weight of 1205 grams, a net increase of 50.6% w/w.

We claim:

1. A process for providing a dry, dust-free particle from an enzyme containing fermentation broth, the process comprising:

a) introducing hydratable core particles into a reaction chamber of a fluidized bed spray-coater or building up hydratable core particles in reaction chamber of a fluidized bed spray-coater;

b) providing a fermentation broth which has been filtered to remove while cells and cell debris therefrom, the broth containing from about 5% to about 100% w/w of the total solids therein of a water soluble enzyme in solution produced in the fermentation broth and a total solids content of about 31% to about 55% in the fermentation broth such that the broth has a viscosity of 10–5,000 cps at room temperature;

c) spraying the broth onto the core particles in the sray-coater and evaporating liquid to leave a film of broth solids coated on the core particles, the broth solids added to the core particles providing a total dry weight gain of from about 1% to about 100% w/w; and d) spraying a coating agent dissolved in liquid on the particles containing the coating of the broth solids from step c) in spray-coater and evaporating liquid to leave the coating agent as a coating over the coating of broth solids such that the total broth solids and coating agent added to the core particles provide a total dry weight gain of from about 1% to about 100% w/w over the initial weight of the uncoated core particles.

2. A process according to claim 1 wherein the enzyme is selected from the group consisting of protease, lipase, cellulase and amylase.

3. An enzyme granule made by the process of claim 1.

* * * * *